US00PP35274P2

(12) United States Plant Patent
van Sambeek

(10) Patent No.: US PP35,274 P2
(45) Date of Patent: Jul. 18, 2023

(54) ***HEUCHERA* PLANT NAMED 'DOHEUGABECI'**

(50) Latin Name: *Heuchera hybrida*
Varietal Denomination: DOHEUGABECI

(71) Applicant: DUMMEN GROUP B.V., De Lier (NL)

(72) Inventor: Ellen van Sambeek, Oegstgeest (NL)

(73) Assignee: DUMMEN GROUP B.V., De Lier (NL)

( * ) Notice: Subject to any disclaimer, the term of this patent is extended or adjusted under 35 U.S.C. 154(b) by 0 days.

(21) Appl. No.: 17/838,965

(22) Filed: Jun. 13, 2022

(51) Int. Cl.
*A01H 5/02* (2018.01)
*A01H 6/80* (2018.01)

(52) U.S. Cl.
USPC ..... Plt./440
CPC ..... *A01H 6/80* (2018.05)

(58) Field of Classification Search
USPC ..... Plt./440
CPC ..... A01H 6/80; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Heuchera* plant named 'DOHEURGABECI', characterized by its compact and uniformly mounded plant habit; moderately vigorous growth habit; densely foliated and bushy appearance; glossy leaves that are initially dark reddish green in color becoming dark green with development; and good garden performance and winter hardiness.

1 Drawing Sheet

Botanical designation: *Heuchera hybrida.*
Cultivar denomination: 'DOHEUGABECI'.

CROSS-REFERENCED TO CLOSELY-RELATED APPLICATIONS

Title: *Heuchera* Plant Named 'DOHEUGABERU'
Inventor: Ellen van Sambeek
Filed: Jun. 13, 2022
Ser. No. 17/838,979

BACKGROUND OF THE INVENTION

The present invention relates to a new and distinct *Heuchera* plant, botanically known as *Heuchera hybrida*, typically grown as a landscape *Heuchera* and hereinafter referred to by the name 'DOHEURGABECI'.

The new *Heuchera* plant is a product of a planned breeding program conducted by the Inventor in Aalsmeer, The Netherlands. The objective of the breeding program is to create new compact *Heuchera* plants with attractive leaf coloration and good garden performance.

The new *Heuchera* plant originated from a cross-pollination of *Heuchera hybrida* 'Obsidian', disclosed in U.S. Plant Pat. No. 14,836, as the female, or seed, parent with *Heuchera hybrida* 'Marmalade', disclosed in U.S. Plant Pat. No. 15,945, as the male, or pollen, parent in June, 2016. The new *Heuchera* plant was discovered and selected as a single plant from within the progeny of the stated cross-pollination in a controlled nursery environment in Aalsmeer, The Netherlands in June, 2017.

Asexual reproduction of the new *Heuchera* plant by vegetative cuttings in a controlled greenhouse environment in Aalsmeer, The Netherlands since July, 2017, has shown that the unique features of this new *Heuchera* plant are stable and reproduced true to type in successive generations.

SUMMARY OF THE INVENTION

The new *Heuchera* plant has not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'DOHEURGABECI'. These characteristics in combination distinguish 'DOHEURGABECI' as a new and distinct *Heuchera* plant:

1. Compact and uniformly mounded plant habit.
2. Moderately vigorous growth habit.
3. Densely foliated and bushy appearance.
4. Glossy leaves that are initially dark reddish green in color becoming dark green with development.
5. Good garden performance and winter hardiness.

Plants of the new *Heuchera* differ primarily from plants of the female parent, 'Obsidian', in leaf color as leaves of plants of the new *Heuchera* are initially dark reddish green in color becoming dark green with development whereas leaves of plants of 'Obsidian' are very dark (almost black) in color.

Plants of the new *Heuchera* differ primarily from plants of the male parent, 'Marmalade', in leaf color as leaves of plants of the new *Heuchera* are initially dark reddish green in color becoming dark green with development whereas leaves of plants of 'Marmalade' are russet to amber in color.

Plants of the new *Heuchera* differ primarily from plants of *Heuchera hybrida* 'DOHEURABERU', disclosed in a U.S. Plant Patent application filed concurrently, in leaf color as leaves of plants of the new *Heuchera* are initially dark reddish green in color becoming dark green with development whereas leaves of plants of 'DOHEURABERU' are initially reddish purple to greenish brown in color becoming yellowish green with development.

Plants of the new *Heuchera* can be also compared to plants of *Heuchera hybrida* 'Amethyst Mist', not patented. In side-by-side comparisons, plants of the new *Heuchera* differ primarily from plants of 'Amethyst Mist' in leaf color as leaves of plants of the new *Heuchera* are initially dark reddish green in color becoming dark green with development whereas leaves of plants of 'Amethyst Mist' are red in color.

BRIEF DESCRIPTION OF THE PHOTOGRAPH

The accompanying colored photograph illustrates the overall appearance of the new *Heuchera* plant showing the colors as true as it is reasonably possible to obtain in colored reproductions of this type. Colors in the photograph may differ slightly from the color values cited in the detailed botanical description which accurately describe the colors of the new *Heuchera* plant.

The photograph is a side perspective view of a typical plant of 'DOHEURGABECI' grown in a container.

DETAILED BOTANICAL DESCRIPTION

The aforementioned photographs and following observations, measurements and values describe plants grown during the autumn in 17-cm containers in a glass-covered greenhouse in Aalsmeer, The Netherlands and under cultural practices typical of commercial *Heuchera* production. During the production of the plants, day temperatures averaged 21° C. and night temperatures averaged 15° C. Plants were one year old when the photograph and the description were taken. In the following description, color references are made to The Royal Horticultural Society Colour Chart, Second Edition, except where general terms of ordinary dictionary significance are used.

Botanical classification: *Heuchera hybrida* 'DOHEURGABECI'.

Parentage:

*Female, or seed, parent.*—*Heuchera hybrida* 'Obsidian', disclosed in U.S. Plant Pat. No. 14,836.

*Male, or pollen, parent.*—*Heuchera hybrida* 'Marmalade', disclosed in U.S. Plant Pat. No. 15,945.

Propagation:

*Type*.—By in vitro meristem culture.

*Time to initiate roots, summer*.—About ten days at temperatures about 26° C.

*Time to initiate roots, winter*.—About two weeks at temperatures about 23° C.

*After rooting, time to produce a rooted young plant, summer*.—About twelve days at temperatures about 23° C.

*After rooting, time to produce a rooted young plant, winter*.—About 16 days at temperatures about 18° C.

*Root description*.—Medium in thickness, fibrous; typically white to light yellow in color, actual color of the roots is dependent on substrate composition, water quality, fertilizer type and formulation, substrate temperature and physiological age of roots.

*Rooting habit*.—Moderately freely branching; dense.

Plant description:

*Plant and growth habit*.—Herbaceous perennial; basal rosette plant habit with leaves developing from the base; densely foliated and dense and bushy appearance; compact and uniformly mounded plant habit; overall shape, flattened globular; moderately vigorous growth habit; slow growth rate.

*Plant height*.—About 18 cm.

*Plant diameter or spread*.—About 36 cm.

Leaf description:

*Arrangement*.—Alternate in basal rosettes; simple.

*Length*.—About 6.5 cm.

*Width*.—About 6.5 cm.

*Shape*.—Broadly ovate; palmately lobed.

*Apex*.—Obtuse.

*Base*.—Cordate.

*Margin*.—Crenate; sinuses medium in depth and divergent; slightly undulate; ciliate.

*Texture and luster, upper surface*.—Smooth, glabrous; glossy.

*Texture and luster, lower surface*.—Smooth, glabrous; slightly glossy.

*Venation pattern*.—Palmate; reticulate.

*Color*.—Developing leaves, upper surface: Initially, close to 59A becoming closer to 59A tinged with 147A with development. Developing leaves, lower surface: Close to 59A. Fully expanded leaves, upper surface: Close to 147A; venation, close to 147A. Fully expanded leaves, lower surface: Close to 147A tinged with close to 59B; venation, close to 147B.

*Petioles*.—Length: About 11 cm. Diameter: About 3 mm. Strength: Moderately strong. Texture and luster, upper and lower surfaces: Pubescent; glossy. Color, upper and lower surfaces: Initially, close to 59A becoming closer to 148A tinged with close to 59A with development.

Flower description: To date, flower initiation and development has not been observed on plants of the new *Heuchera*.

Pathogen & pest resistance: To date, plants of the new *Heuchera* have not been observed to be resistant to pathogens and pests common to *Heuchera* plants.

Garden performance: Plants of the new *Heuchera* have been observed to have good garden performance and to tolerate temperatures ranging from about −29° C. to about 35° C. and to be suitable for USDA Hardiness Zones 5 through 10.

It is claimed:

1. A new and distinct *Heuchera* plant named 'DOHEURGABECI' as illustrated and described.

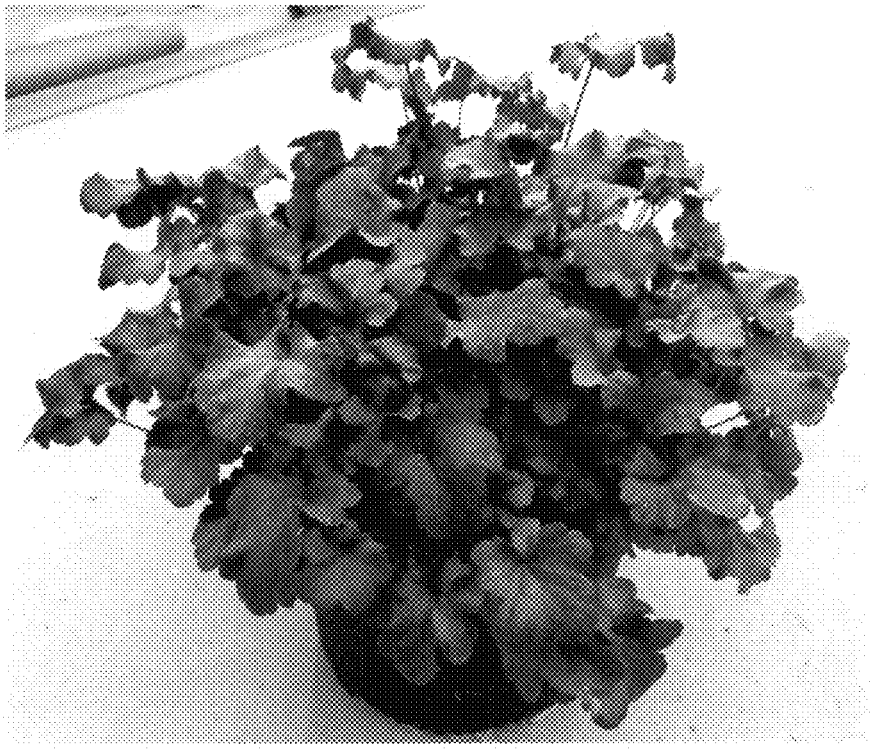

* * * * *